United States Patent
Golz-Berner et al.

(10) Patent No.: US 7,338,671 B2
(45) Date of Patent: Mar. 4, 2008

(54) SKIN-SMOOTHING COSMETIC BASED ON PLANT EXTRACTS

(75) Inventors: Karin Golz-Berner, Monaco (MC); Leonhard Zastrow, Monaco (MC)

(73) Assignee: Coty B.V. (NL)

( * ) Notice: Subject to any disclaimer, the term of this patent is extended or adjusted under 35 U.S.C. 154(b) by 598 days.

(21) Appl. No.: 10/523,082

(22) PCT Filed: Aug. 16, 2002

(86) PCT No.: PCT/DE02/03059

§ 371 (c)(1),
(2), (4) Date: Feb. 2, 2005

(87) PCT Pub. No.: WO2004/017934

PCT Pub. Date: Mar. 4, 2004

(65) Prior Publication Data

US 2005/0255077 A1     Nov. 17, 2005

(51) Int. Cl.
*A01N 65/00*     (2006.01)

(52) U.S. Cl. .................................................. 424/725

(58) Field of Classification Search ................... None
See application file for complete search history.

(56) References Cited

FOREIGN PATENT DOCUMENTS

JP         63303908     * 12/1988

* cited by examiner

*Primary Examiner*—Michael Meller
(74) *Attorney, Agent, or Firm*—Stephan Pendorf; Akerman Senterfitt

(57) ABSTRACT

The invention relates to a cosmetic whose active constituents are specified plant extracts and which has a very good skin-smoothing activity. According to the invention, the skin-smoothing of porous or uneven skin having macroscopically visible elevations and depressions during cosmetic processes occurs without irritating side effects. The cosmetic contains plant extracts from *Bambusa vulgaris, Nymphaea alba, Poterium officinale, Zingiber officinalis, Cinnamomum cassia, Nasturtium officinale* R.Br., *Nelumbo nucifera* Gaertn. and contains a powder selected from the group consisting of talcum powder, bamboo powder, kaolin, zinc oxide and mixtures thereof. The inventive cosmetic also contains cosmetic adjuvants, excipients, additional active substances and mixtures thereof.

6 Claims, No Drawings

SKIN-SMOOTHING COSMETIC BASED ON PLANT EXTRACTS

CROSS REFERENCE TO RELATED APPLICATION

This application is a national stage of PCT/DE2002/003059 filed Aug. 16, 2002.

BACKGROUND OF THE INVENTION

1. Field of the Invention

The invention relates to a cosmetic whose active constituents are specified plant extracts and which has a very good skin-smoothing activity.

2. Related Art of the Invention

A number of cosmetic products are known which have an anti-inflammatory activity on the skin. DE 199 33 857, for example, discloses a cosmetic containing extracts from plants of the Piperaceae family. It is further known from a plurality of patents and other publications that vitamins and antioxidants can be used to prevent signs of ageing and for skin care. It is also known that new epidermal cells will form due to the use of fruit acids (AHA acids; AHA effect), thus contributing to skin regeneration; however, this method is much disputed because of its side effects.

SUMMARY OF THE INVENTION

The object of the invention is to provide a cosmetic without irritating side effects which is suitable for smoothing porous or uneven skin having macroscopically visible elevations and depressions.

According to the invention, the aforesaid object is achieved by means of a cosmetic with a plant extract base. Said cosmetic consists of
- 0.01 to 10% by weight of an extract from the leaves and stems of *Bambusa vulgaris* (bamboo milk);
- 0.01 to 5% by weight of an extract from the roots of *Nymphaea alba;*
- 0.01 to 5% by weight of a mixture of extracts from the roots of *Poterium officinale* (also known as *Sanguisorba officinalis*) and from the roots of *Zingiber officinalis* and from the bark of *Cinnamomum cassia;*
- 0.01 to 5% by weight of an extract from the entire plant of *Nasturtium officinale* R.Br.;
- 0.01 to 5% by weight of an extract from the flowers of *Nelumbo nucifera* Gaertn.;
- 0.01 to 20% by weight of a powder selected from the group consisting of talc, bamboo powder, kaolin, zinc oxide and mixtures thereof; and
- 20 to 95% by weight of cosmetic adjuvants, excipients, additional active substances and mixtures thereof, all percentages being relative to the cosmetic's weight.

Bamboo milk is an extract obtained mainly from the leaves of *Bambusa vulgaris* which also comprise parts of the stems. Said leaves are subjected to an extraction with aqueous propylene glycol in order to obtain both water-soluble and fat-soluble constituents, particularly vitamins, saponins, tannins of phenolic acids such as caffeic acid and gallic acid, constituents containing silicic acid, minerals, sterols such as sitosterol, stigmasterol and α-amyrin, and flavonoids. The overall mixture, which is provided in aqueous propylene glycol and can optionally also be incorporated into the cosmetic composition in a dry form (e.g. spray-dried), has a skin-cleansing, draining, astringent and anti-inflammatory activity. Bamboo milk preferably makes up 0.1 to 5% by weight, particularly 1 to 5% by weight.

The extract from *Nymphaea alba* is an orange liquid whose pH value ranges between 4.0 and 6.0 and whose density is 1.035-1.055 at 20° C. Extraction is done using a mixture of water and propylene glycol at a ratio ranging between 40:60 and 60:40. The root extract is soluble in water and 60% ethanol. It contains alkaloids, flavonoids and ascorbic acid, thus having an antibacterial, tonifying and anti-inflammatory activity. This extract preferably makes up 0.1 to 5% by weight, particularly 1 to 5% by weight.

The mixture of extracts from the roots of *Poterium officinale*, from the roots of *Zingiber officinalis* and from the bark of *Cinnamomum cassia* contains each of its individual constituents in an amount ranging between 20 and 40% by weight, relative to the dry weight of the raw materials used. The root extract from *Poterium officinale* is obtained using a mixture of water and butylene glycol, the extracts from *Zingiber officinalis* and from the bark of *Cinnamomum cassia* are obtained using water. The extract mixture has mainly an antibacterial and an astringent effect. The extract contains essential oils, saponosides, triterpenes and tannins. It is a translucent, red/orange solution in aqueous butylene glycol, has a pH value ranging between 4.0 and 6.0 and a density of 1.010-1.040, is mixable with water, propylene glycol and 50% ethanol and non-mixable with mineral oils. Said extract mixture preferably makes up 0.1 to 5% by weight, particularly 1 to 5% by weight.

The extract from *Nasturtium officinale*, which is obtained from the entire plant using aqueous propylene glycol, has a chestnut/orange colour, a density of 1.035-1.055 at 20° C. and is soluble in water and alcohol. It has an antibacterial and tonifying effect. Said effect can probably be attributed to the fact that the extract contains trace elements, carotenoids, essential oils and ascorbic acid. Said extract preferably makes up 0.1 to 5% by weight, particularly 1 to 5% by weight.

The extract from *Nelumbo nucifera* Gaertn. (or *Nelumbium nelumbo* Druce), which is obtained from the flowers using aqueous propylene glycol, has a chestnut/orange colour, a density of 1.02-1.060 at 20° C. and is soluble in water and alcohol. It contains an amino acid mixture, ascorbic acid and flavonoids. Said extract preferably makes up 0.1 to 5% by weight, particularly 1 to 5% by weight.

The overall mixture in the form of the inventive cosmetic shows an astringent, skin-clearing activity and, in particular, counteracts uneven spots in the skin such as small pimples, i.e. the skin becomes extraordinarily smooth in a very short time. It is particularly surprising that such a broad effect is achieved so quickly. The skin is not irritated in any way, the aforedescribed effect is achieved in a very skin-gentle manner and bacterial lipase is clearly inhibited by the combination.

In one embodiment, the cosmetic can further contain 0.01 to 5% by weight of an extract from *Epilobium angustifolium* or a product containing said extract, e.g. Seborilys® marketed by Greentech, St. Beauzire, France. Such a product inhibits 5α-reductase, thus influencing the enzyme activity, and shows a certain anti-androgenic activity due to macrocyclic tannins.

A preferred powder combination in the aforesaid composition consists of 8-15% talc, 15-24% bamboo powder, 40-58% kaolin and 15-25% zinc oxide. Said kaolin can be kaolin according to WO96/17588 which has been modified with spherical $TiO_2$ or $SiO_2$ particles whose particle size is <5 μm, the spherical particles making up 0.5 to 10% by weight of the kaolin mixture. In this way, the preparation will feel very soft on the skin and have an additional anti-inflammatory activity.

The bamboo powder used preferably consists of the powdered medulla of Bambusa arundinacea having a preferred medium particle size of approx. 5 µm, approx. 60% of the particles ranging between 2 an 6 µm. This particular bamboo species is native to some Indian mountain woods and is particularly suitable for absorbing sebum and texturizing cosmetic products. A particularly preferred product is Greensil® marketed by Greentech, St. Beauzire, France. The inventive cosmetic can preferably contain bamboo powder alone.

The powder preferably makes up 0.1 to 20% by weight of the mixture, particularly 5 to 20% by weight.

In one embodiment of the invention, a powder consisting of methyl methacrylate/ethylene glycol bismeth-acrylate copolymer can also be added, which powder has an average particle size of approx. 8 µm and is provided in the form of macroporous globules. The PMMA powder can make up 0.5 to 10% by weight.

The powder contained in the composition absorbs sweat and at the same time acts as a cover, i.e. it prevents oxygen from reaching the uneven spots in the skin so that the bacterial activity is not stimulated even more.

The inventive cosmetic can further contain cosmetic adjuvants and excipients as they are commonly used in such preparations, e.g. water, preservatives, vitamins, colourants, pigments, free radical scavengers, thickeners, emollients, fragrances, alcohols, polyols such as glycerine and propylene glycol and butylene glycol, esters or ethers, electrolytes, polar and non-polar oils, polymers, copolymers, emulsifiers, waxes, gels, stabilizers, amines such as triethanolamine, or mixtures thereof.

Pigments, pigment mixtures or powders having a pigment-like effect, including those having a pearlescent effect, can include e.g. iron oxides, natural aluminosilicates such as ochre, titanium (di)oxide, mica, kaolin, clays containing manganese such as umber and red bole, calcium carbonate, talc, mica-titanium oxide, mica-titanium oxide-iron oxide, bismuth oxy-chloride, nylon globules, ceramic globules, expanded and non-expanded synthetic polymer powders, powdery natural organic compounds such as ground solid algae, ground parts of plants, encapsulated and non-encapsulated cereal starches and mica-titanium oxide-organic colourant.

Suitable esters or ethers include e.g. (INCI names): Dipentaerythrityl hexacaprilate/hexacaprate/tridecyl tri-mellitate/tridecyl stearate/neopentyl glycol dicaprylate dicaprate, Propylene glycol dioctanoate 5, Propylene glycol di-caprylate 2,30 dicaprate, Tridecyl stearate/neopentyl glycol dicaprylate dicaprate/tridecyl trimellitate, Neopentyl glycol di-octanoate, Isopropyl myristate, Diisopropyl dimer dilinoleate, Trimethylpropane triisostearate, Myristyl ether, Stearyl ether, Cetearyl octanoate, Butyl ether, Dicaprylyl ether, PPG1-PEG9 Lauroyl glycol ether, PPG15 Stearyl ether, PPG14 Butyl ether, PEG20 Stearate, PEG100 Stearate, Fomblin HC25.

Cosmetic oils used in small amounts, e.g. ranging below 5% by weight, can be vegetable oils such as calendula oil, jojoba oil, avocado oil, macadamia nut oil, castor oil, wheatgerm oil, grapeseed oil, kukui nut oil, thistle oil, evening primrose oil, safflower oil or a mixture of several thereof. Mineral oils can also be used.

Suitable water- and/or oil-soluble UVA or UVB filters or both can be added to the inventive compositions. Advantageous oil-soluble UVB filters include derivatives of 4-aminobenzoic acid such as 4-(dimethylamino)-benzoic acid-(2-ethylhexyl) ester; esters of cinnamic acid such as 4-methoxycinnamic acid(2-ethylhexyl) ester; benzophenone derivatives such as 2-hydroxy-4-methoxybenzophenone; derivatives of 3-benzylidene camphor such as 3-benzylidene camphor.

Preferred oil-soluble UV filters are Benzophenone-3, Butyl Methoxybenzoylmethane, Octyl Methoxycinnamate, Octyl Salicylate, 4-Methylbenzylidene Camphor, Homosalate and Octyl Dimethyl PABA.

Water-soluble UVB filters include e.g. sulphonic acid derivatives of benzophenone or of 3-benzylidene camphor, or salts such as the Na or K salt of 2-phenylbenzimidazol-5-sulphonic acid.

UVA filters include derivatives of dibenzoylmethane such as 1-phenyl-4-(4'-isopropylphenyl)propane-1,3-dione.

Preferred sunscreens are inorganic pigments based on metal oxides such as $TiO_2$, $SiO_2$, $ZnO$, $Fe_2O_3$, $ZrO_2$, $MnO$, $Al_2O_3$, mixtures of which can also be used.

Particularly preferred inorganic pigments are agglomerated substrates of $TiO_2$ and/or $ZnO$, which substrates contain spherical and porous $SiO_2$ particles whose particle size ranges between 0.05 and 1.5 µm and, in addition to said $SiO_2$ particles, other inorganic, particle-shaped substances having a spherical structure, said spherical $SiO_2$ particles combining with said other inorganic substances to form defined agglomerates whose particle size ranges between 0.06 and 5 µm (according to WO99/06012).

It is also preferred that a product obtained by ultrasonic decomposition of a yeast be contained as an additional active substance, which decomposition product contains superoxide dismutase (SOD), protease, vitamin $B_2$, vitamin $B_6$, vitamin $B_{12}$, vitamin $D_2$ and vitamin E. Preferably, said product contains at least 150 IU/ml SOD, protease and vitamins B and D, the ratio of SOD to protease, expressed in international units, ranging at least between 3:1 and 8:1.

It is particularly advantageous that said decomposition product, i.e. an enzyme/vitamin mixture, be obtained by means of an ultrasonic decomposition process as described in DE 4241154C1 (U.S. Pat. No. 5,629,185A is an English language document in the patent family of DE 4241154C1).

The inventive cosmetic preparation can e.g. be used in suncreams, sun gels, after-sun products, day creams, night creams, masks, body lotions, cleansing milk, make-up, lipsticks, body powder, eye cosmetics, hair masks, hair conditioners, hair shampoos, shower gels, shower oils, bath oils. The aforesaid products are manufactured in a way known to those skilled in the art.

The invention will hereinafter be explained in more detail by means of examples. All quantities are in % by weight unless indicated otherwise.

EXAMPLE 1

Coloured Anti-Pimple Cream

| Phase A | |
|---|---|
| Stearyl alcohol | 2.5 |
| Cetearyl Octanoate | 4.3 |
| Mineral oil | 0.6 |
| Pigments | 3.5 |

-continued

| Phase B | |
|---|---|
| Water | q.s. ad 100 |
| Propylene Glycol | 2.0 |
| Phase C | |
| Bamboo milk extract (dry) | 5.0 |
| *Nymphaea alba* extract | 3.0 |
| Mixture of extracts from *Poterium officinale, Zingiber officinalis* and *Cinnamomum cassia* | 5.0 |
| Extract from *Nasturtium officinale* R.Br. | 0.01 |
| Extract from *Nelumbo nucifera* Gaertn. | 2.0 |
| Powder combination: 10% talc, 20% bamboo powder, 50% kaolin according to WO99/06012, 20% ZnO | 10.0 |
| Decomposition product according to DE 4241152 obtained from *Saccharomyces cerevisiae* | 0.1 |
| Phase D | |
| Preservative | 0.5 |

Phases A and B are prepared separately by mixing the respective ingredients while stirring. Both phases are combined at 75° C.±5° C. and homogenized for 20 min. Subsequently, the mixture is cooled down to 40° C.±2° C., phase C is added and homogenized. Finally, phase D is added.

EXAMPLE 2

Skin-Smoothing Compact Powder I

| Kaolin according to WO99/06012 | ad 100 |
|---|---|
| Talc | 5.0 |
| Bamboo milk extract (dry) | 10.0 |
| *Nymphaea alba* extract | 5.0 |
| Mixture of extracts from *Poterium officinale, Zingiber officinalis* and *Cinnamomum cassia* | 5.0 |
| Extract from *Nasturtium officinale* R.Br. | 5.0 |
| Extract from *Nelumbo nucifera* Gaertn. | 2.0 |
| Powder combination: 10% talc, 20% bamboo powder, 50% kaolin according to WO99/06012, 20% ZnO | 20.0 |
| Emulsion consisting of 93% water, 5% PEG100 Stearate and 2% Cetearyl Isononanoate | 30.0 |

EXAMPLE 3

Skin-Smoothing Compact Powder II

Composed as in Example 1, except that, in addition, 2% of a decomposition product obtained from *Saccharomyces cerevisiae* according to DE 4241152 (U.S. Pat. No. 5,680,010A is an English language document in the patent family of DE 4241152) is used.

The powders according to Examples 2 and 3 were produced by mixing all constituents except the emulsion. In order to prepare the emulsion, the water and the oil phase were heated separately up to approx. 70° C., combined while stirring and cooled down to approx. 40° C. The highly liquid emulsion was then sprayed onto the powder mixture while agitating the latter, mixed thoroughly and the mixture was finally pressed into containers suitable for sale.

EXAMPLE 4

Comparison

The cream according to Example 1 was made available to 12 test persons aged 18 to 55 years. The skin of these persons' faces and necks was uneven with occasional pimples and large pores, and they had regularly used other skin-cleansing cosmetics.

Said test persons were asked to apply the cream evenly and thinly onto their facial and neck skin in the mornings and evenings.

The changes were evaluated using a scale of 1 to 5:
1=no significant change in the skin's appearance
2=small change, contraction of pores
3=acceptable improvement of the skin's smoothness, contraction of pores, pimples in part levelled to some extent
4=clear improvement of the skin's smoothness, contraction of pores, most pimples clearly reduced
5=extraordinary improvement of the skin's smoothness, pimples levelled almost completely, even skin surface In addition, the participants completed a questionnaire asking about ease of application and side effects, among other things. After 4 days, 2 of the 12 test persons judged the change corresponded to "3", 6 test persons chose "4" and 4 test persons chose "5". After 7 days, 1 test person just the change corresponded to "3", 7 test persons chose "4" and 5 test persons chose "5".

This result shows an unexpectedly rapid effect in most test persons and an excellent overall effect after 7 days, while at the same time all test persons confirmed that application was easy and had no side effects.

Said result is even more surprising as individual constituents of the cosmetic, which had been tested earlier using several other test persons, brought about a certain improvement of the skin's appearance, but only after a longer period of application lasting 10 to 30 days.

The invention claimed is:
1. A skin-smoothing cosmetic comprising:
 (a) 0.01 to 10% by weight of an extract from leaves and stems of *Bambusa vulgaris;*
 (b) 0.01 to 5% by weight of an extract from roots of *Nymphaea alba;*
 (c) 0.01 to 5% by weight of a mixture of extracts from roots of *Poterium officinale*, from the roots of *Zingiber officinalis* and from bark of *Cinnamomum cassia;*
 (d) 0.01 to 5% by weight of an extract from an entire plant of *Nasturtium officinale* R.Br.;
 (e) 0.01 to 5% by weight of an extract from flowers of *Nelumbo nucifera* Gaertn.;
 (f) 0.01 to 20% by weight of a powder selected from the group consisting of talc, bamboo powder, kaolin, zinc oxide and mixtures thereof; and
 (g) 20 to 95% by weight of cosmetic adjuvants, excipients, additional active substances and mixtures thereof, all percentages being relative to the weight of the cosmetic.

2. The skin-smoothing cosmetic according to claim 1, wherein said extracts (b) to (e) each make up 0.1 to 5% by weight, said extract (a) makes up 0.1 to 10% by weight, and said powder (f) makes up 5 to 20% by weight.

3. The skin-smoothing cosmetic according to claim 1, wherein said cosmetic additionally contains 0.01 to 2% by weight of a product comprising superoxide dismutase (SOD), protease, vitamin $B_2$, vitamin $B_6$, vitamin $B_{12}$, vitamin $D_2$ and vitamin E.

4. The skin-smoothing cosmetic according to claim 1, wherein said cosmetic additionally contains 0.01 to 5% by weight of an extract from *Epilobium angustifolium* or of a product containing said extract.

5. The skin-smoothing cosmetic according to claim 1, wherein said powder (f) is a powder mixture consisting of 8-15% talc, 15-24% bamboo powder, 40-58% kaolin and 15-25% zinc oxide, relative to the weight of the powder mixture.

6. The skin-smoothing cosmetic according to claim 5, wherein said bamboo powder consists of powdered medulla of *Bambusa arundinacea* having a medium particle size of 5 μm.

* * * * *